United States Patent [19]
Schulze

[11] Patent Number: 4,895,156
[45] Date of Patent: Jan. 23, 1990

[54] SENSOR SYSTEM USING FLUOROMETRIC DECAY MEASUREMENTS

[76] Inventor: John E. Schulze, 1450 Cortez de Prima Vera, Thousand Oaks, Calif. 91360

[21] Appl. No.: 881,139
[22] Filed: Jul. 2, 1986
[51] Int. Cl.[4] .................................................. A61B 5/00
[52] U.S. Cl. .................................... 128/634; 128/633; 128/665; 128/736; 436/172; 250/458.1; 73/1 G; 374/1; 374/161
[58] Field of Search ............... 128/633, 634, 664, 665, 128/666; 436/172; 250/458.1, 459.1; 73/1 G; 374/1, 161

[56] References Cited

U.S. PATENT DOCUMENTS

| | | |
|---|---|---|
| Re. 31,879 | 5/1985 | Lubbers . |
| 2,551,650 | 5/1951 | Urbach . |
| 3,612,866 | 10/1971 | Stevens . |
| 4,223,226 | 9/1980 | Quick . |
| 4,245,507 | 1/1981 | Samulski . |
| 4,374,328 | 2/1981 | Tekippe . |
| 4,437,772 | 1/1981 | Samulski . |
| 4,476,870 | 10/1984 | Peterson . |
| 4,592,361 | 6/1986 | Parker et al. ........................ 128/634 |
| 4,606,351 | 8/1986 | Lubbers ............................. 128/665 |
| 4,675,529 | 6/1987 | Kushida ............................. 128/665 |
| 4,810,655 | 3/1989 | Khalil et al. ........................ 128/633 |

FOREIGN PATENT DOCUMENTS

| | | |
|---|---|---|
| 87/00023 | 1/1927 | PCT Int'l Appl. . |
| 2132348 | 4/1984 | United Kingdom . |

OTHER PUBLICATIONS

Bergman, Rapid-Response Atmospheric Oxygen Monitor Based on Fluorescence Quenching, NATURE, 218, 396, Apr. 1968.
Birks, J. B. and Dyson, D. J., Phase and Modulation Fluorometer., J. of Science Instrument., 38, Jul. 1961.
Demas, J. N., Luminescence Decay Times and Bimolecular Quenching, J. Chem. Ed., 53, 10, 1976.
Demas, J. N., Luminescence Spectroscopy and Bimolecular Quenching, J. Chem. Ed., 52, 10, 1975.
Demas, J. N. and Flynn, C. M. Jr., Inexpensive Laser Luminescence Decay Time Apparatus, Anal. Chem., 48, 2, 1976.
Fisher, R. P. and Winefordner, J. D., Pulsed Source-Time Resolved Phosphorimetry, Analytical Chemistry, 44, 6, 1972.
Gehrich, Lubbers et al., Optical Fluorescence and Its Application to an Intravascular Blood Gas Monitoring Systems, IEEE Trans., Biomed. Eng., BME-33, 2, 1986.
Gratton, E. and Limkeman, M., A Continuously Variable Frequency Cross-Correlation Phase Fluorometer with Picosecond Resolution, Biophys., J., 44, Dec. 1983.
Gruneis, F., Schneider, S. and Dorr, F., Phase Fluorimetry with Variable Duty Cycle Electrical' Phosphoroscope, J of Physics E: Scientific Instruments, 9, 1013-1017, 1976.
Hauser, M., Heidt, G., Phase Fluorometer with a Continuously Variable Frequency, Rev. Scientific Instruments, 46, 4, 1975.
James, K. A., Quick, W. H. and Strahan, V. H., Analysis and Preliminary Design of Optical Sensors for Production Control, NTIS Report, #N79-27975, U.S. Dept. Commerce, Jan. 1979.
Lytle, F. E., Eng, J. F., Harris, J. M., Harris, T. D. and Santini, R. E., Spectroscopic Excitation Source with Variable Frequencies and Shapes of Modulation, Anal. Chem., 47 3, 1975.
Sholes, R. R., Fluoroescent Decay Thermometer with Biological Applications.
Wickersheim et al., Recent Advances in Optical Temperature Measurement, Industrial Research and Development, Dec. 1979.

Primary Examiner—Kyle L. Howell
Assistant Examiner—John C. Hanley
Attorney, Agent, or Firm—Watts, Hoffmann, Fisher & Heinke

[57] ABSTRACT

A body fluid component and/or temperature monitoring system including a fiber optic catheter, fluid monitoring probe at the distal end of the catheter, pulsed light source for exciting the probe, and photosensor for responding to light coming from the distal end of the catheter. Circuitry analyzes the light output from the probe and determines a time delay that characterizes the body fluid component concentration or temperature. The time decay is then preferably converted to either component concentration or temperature and displayed on a visual display.

24 Claims, 4 Drawing Sheets

SENSOR SYSTEM USING FLUOROMETRIC DECAY MEASUREMENTS

TECHNICAL FIELD

This invention relates to photoluminescent indicators and in particular to a pulsed fluorometric sensor system for measuring oxygen partial pressure, pH, $CO_2$ or temperature at a tip of a fiber optic-equipped catheter in an organ or a body.

BACKGROUND ART

It has long been known that many photoluminescent materials exhibit substantial reductions in their luminescent intensities or luminescent decay lifetimes as a result of increases in the temperature of the material. These characteristics have been exploited in the development of various fiber optic temperature sensor probes (See Urbach, U.S. Pat. No. 2,551,650, Samulski, U.S. Pat. Nos. 4,437,772, 4,245,507, Quick U.S. Pat. No. 4,223,226, Wickersheim, et al., (Recent Advances in Optical Temperature Measurement, Industrial Research & Development, December, 1979), Sholes, et al., (Fluorescent Decay Thermometer with Biological Applications, Rev. Sci. Instrum., 51, 7 July , 1980), and Tekippe, U.S. Pat. No. 4,374,328.

For some luminescent materials, "quenching" (i.e., reductions in luminescent intensity) due to the presence of oxygen molecules (see Bergman, Rapid-response Atmospheric Oxygen Monitor based on Fluorescence Quenching, Nature 218, 396, Stevens, U.S. Pat. No. 3,612,866, Lubbers, U.S. Pat. Re. 31,879, Peterson U.S. Pat. No. 4,476,870, and Cox, "Detection of $O_2$ by fluorescence quenching", Applied Optics/ 24, 14, 1985) has been exploited for the construction of fluorometric probes.

Further, the presence of the hydrogen ion can sensitively quench some luminescent materials (see Lubbers U.S. Pat. Re. 31,879, and Saari, et al., "pH sensor based on immobilized fluoresceinamine", Anal. Chem. 1982, 54, 821-3), as can a variety of other chemical quenching species, such that it is possible to measure the concentrations of such quenching species via "fluorometric sensors". (See Harte, U.S. Pat. No. 3,992,631).

Generally, it can be stated that fluorescence quenching (i.e., using reductions in intensity of emission of a photoluminescent material to measure concentration of a quenching species) is a well established methodolgy in analytical chemistry.

However, direct measurement of the photoluminescent lifetimes of those materials suitable or useful for assay of chemical species such as the oxygen molecule or hydrogen ion or other blood gasses has generally been reserved for the research laboratory, and such techniques have not been used in the field of fiber optic sensors which are placed in a remote environment. This has been true for several reasons: (1) The photoluminescent lifetimes of suitable materials is generally quite short. For instance, Lubbers teaches the use of Parylene Dibutyric Acid and Beta Methyl Umbelliferone; Cox, the use of 9, 10 Diphenyl Anthracene. Other examples are cited in the referenced prior art. The photoluminescent lifetime of such species is on the order of 10 nanoseconds, and generally with required excitation wavelengths in the ultraviolet. In order to accomplish lifetime measurements on such specie a large, expensive excitation light source has been required such as a gas ion laser with internal or external modulation capabilities in the nanosecond (Gigahertz) range. (2) Photosensor systems for detecting and analyzing such high speed luminescent decays whether by direct pulse contour analysis (see Lackowicz, Principles of Fluorescence Spectroscopy, Chapter 3, Plenum Press, New York 1983, and Gafni, et al., Analysis of Fluorescence Decay Curves by Means of the Laplace Transformation, Biophysical Journal, 15, 1975) or by analysis of the emitted luminescent response to a modulated excitation source (see Lackowicz, Chapter 3 & 4; Gratton, et al., A continuously Variable Frequency Cross-Correlation Phase Fluorometer with Picosecond Resolution, Biophysical Journal, 44, December, 1983; Lytle, et al., Spectroscopic Excitation Source with Variable Frequencies and Shapes of Modulation, Anal. Chem. 47, 3, 1975; Hauser, et al., Phase Fluorometer with a continuously variable frequency, Rev. Sci. Instrum., 46, 4, 1975, and Birks, et al., Phase and Modulation fluorometer, J. Sci. Instruments, 38, July, 1961) are again expensive and bulky, and subject to considerable detection errors as a result of minor changes in the pulse shape or modulation characteristic of the light source.

As a result of the foregoing size, sophistication, and expense of laboratory lifetime measurement apparatus, previous workers in the field of catheter-based fiber optic sensing systems for the detection of oxygen and other fluid components in the body have relied upon the measurement of quenching—i.e., the reduction in average luminescent intensity of the fluorometric sensor due to the presence of the quenching fluid component upon application of a precisely regulated, continuous source of excitation light. However, there are definite advantages to the measurement of luminescent lifetimes as opposed to quenching intensities in the field of catheter-based fiber optic sensors:

(1) Flexing of the catheter and fiber optic as normally occurs in catheter applications causes a reduction in quench/intensity which can be interpreted by the user as a change in the quencher concentration at the tip of the catheter. Lifetime measurement, which is not dependent on the absolute intensity of luminescence transmitted through the fiber optic light pipe, does not suffer from this drawback.

(2) A fiber optic sensor probe employing lifetime measurements could be easily disconnected and reconnected to a lifetime measurement apparatus without concern for recalibration of the apparatus due to chanes in the attenuation of the intervening fiber optic connector. This is a significant practical advantage in critically ill patients who undergo many tests and procedures.

(3) During operation, a fluorometric sensor normally suffers some reduction in luminescent intensity output due to photo-destruction of the luminescent material by the incident light source. This source "drift," in an intensity measurement system, can be interpreted by the user as an increase in quencher concentration at the tip of the catheter. Lifetime measurement systems do not suffer from "drift" due to slow photo-destruction or bleaching of the luminescent material since they are not sensitive to quench intensity variations.

In an article entitled "Phase fluorimetry with a variable duty cycle electrical phosphoroscope," Gruneis, et al., discloses a mechanically-chopped light source used in conjunction with a synchronized electrically gated photosensor to separate out and measure the decay curve of the relatively long-lived phosphorescence component of a luminescent material while eliminating strong short term interference from the light source and from an accompanying fluorescent emitted component from the material. The area under the remaining long term decay curve is integrated and used with a single-exponent mathematical model to indirectly estimate phosphorescent lifetime.

Fisher and Winefordner (Pulsed Source-Time Resolved Phosphorimetry, Analytical Chemistry, 44, 6, 1972) disclose phosphorimeters wherein time-delayed, gated detectors integrate the phosphorescent response to a pulsed light source ot obtain an indication of the lifetime of organic phosphors.

James, et al. (Analysis and Preliminary Design of optical sensors for propulsion control, NTIS Report #N79-27975, U.S. Dept. Commerce, January, 1979) describes the construction of pulsed, luminescent, fiber optic temperature sensor wherein the time required for the sensor's luminescence to decay from a normalized initial intensity to a specified fraction thereof is measured and related to temperature.

Sholes (Fluorescent decay thermometer with biological applications, Rev. Sci. Instrum., 51 (7), 1980) excites the long-lived fluorescence of ruby with a short pulse of light and integrates precisely-timed portions of the resulting decay curve after a predetermined threshold point to develop a computation which is said to be related to the temperature of the sensor. Sholes specifically teaches against sampling of the decay curve because of problems with D.C. shift and noise in the amplifier/detector and variations in the light source intensity.

Samulski (U.S. Pat. No. 4,245,507) proposes a fiber optic probe for temperature sensing in the human body and recognizes that the sensor's luminescent output could be analyzed via pulse decay or phase shift techniques, but fails to describe how such an analysis system might be constructed.

In pending British patent application No. 2132348A, Demas, et al., describes a group of organometallic compounds suitable for use as fluorescent oxygen sensors when embedded in polymer matrixes. Demas discloses that these materials could be used in conjunction with intensity or lifetime analysis techniques for construction of a fiber optic oxygen sensor system for use inside the body. Demas has also described (see Luminescence Spectroscopy and Bimolecular Quenching, J. Chem. Ed., 52, 10, 1975; Luminescence Decay Times and Bimolecular Quenching, J. Chem. Ed., 53, 10, 1976, and Inexpensive Laser Luminescence Decay Time Apparatus, Anal. Chem., 48, 2, 1976) two decay time analysis systems which are said to be inexpensive means for measuring the lifetimes of the referenced organometallics or of other luminescent materials. The first system uses a flashlamp, and the second a pulsed-nitrogen laser to deliver a pulse of excitation light to the luminescent material, whereupon, the resulting luminescent decay is detected and analyzed by graphical methods using a storage oscilloscope.

Each of the foregoing prior art techniques has its own drawback and limitation with respect to construction of fiber optic temperature or fluid component sensors for use inside the body and in body fluids, and for an accessory lifetime measurement appartus.

The instruments of Gruenis, et al., and Fisher, et al. fairly represent the current state of the art in Time-Resolving Phosphorimeters, wherein the area under a phosphorescent decay curve of a phosphor material located in a sample compartment is integrated over a predetermined time interval following the extinction of an excitation lamp, whereupon the integral is related to the lifetime of the phosphor.

These laboratory instruments are incapable of measuring fluorescent decays—which are 1000 times or more faster than phosphorescent decays, and in fact the authors teach that it is an advantage that the instruments are insensitive to such faster fluorescent decays. In addition, such instruments are not constructed or proposed for use with fiber optic sensors placed in remote environments.

The signal analysis techniques of James, et al. and Quick, U.S. Pat. No. 4,223,226, in a fiber optic temperature sensor system, require the decay curve of a phosphor to decline to a preset threshold, whereupon a timer is started and then stopped when the decay further declines to a second predetermined threshold. However, since fluoescent decays are very fast, noisy phenomena, it is difficult if not impossible to measure such thresholds accurately. The temperature sensor system of Sholes similarily depends upon the on-line sensing of a preset threshold before curve integration can begin.

None of workers in the field of fiber optic temperature sensors have proposed that pulse decay-curve analysis techniques described in the prior art are suitable or usable for the development of oxygen or pH sensor probes.

The first apparatus reported by Demas uses a flashlamp with a relatively long and unpredictable decay characteristic. Demas' results with this device depend on tedious curve tracing and deconvolution techniques which result in considerable experimental errors. The second apparatus of Demas uses a nitrogen laser which is expensive and difficult to maintain. Results still depend on manual curve tracing, graphical analysis, and the services of an off-line computer.

DISCLOSURE OF THE INVENTION

It is accordingly an object of the present invention to overcome the defects in the prior art. It is a further object of the present invention to provide a fluorometric sensor system for the analysis of temperature, oxygen, or other body constituents based upon fluorescent lifetime measurements and employing a fiber-optic equipped catheter. A still further object of the present invention is to provide a relatively inexpensive apparatus for measurement of fluorescence lifetimes outside the research laboratory. A still further object of the present invention is to provide a temperature-compensated fluid-component sensor system using a fluorometric sensor.

The invention comprises a pulsed, fluorometric sensor system wherein a pulse generator having multiple, time-related output pulses has a first output pulse which excites a pulsed light source. The light source emits a short pulse of light, at least a portion of which is in the upper portion of the visible or long ultraviolet light spectrum. The light pulse is conveyed via a first light path through a coupler and then to a fiber-optic equipped catheter. The catheter has near its distal end, a fluorometric sensor which emits a fluorescent output in response to the pulse of excitation light. The fluorescent output is conveyed via the catheter, coupler, and a second light path to a photosensor. A time dependent output of the photosensor is analyzed via sample and hold and/or curve integration techniques to obtain signals which can be used to determine the lifetime of the fluorometric sensor's decay, which is sensitively responsive to a quencher or the temperature in the sensor's environment. Additional processing of the lifetime signal results in a display which is a functionally related to the temperature or fluid component concentration at the tip of the catheter.

The structure and operation of the invention together with additional objects and advantages thereof will be best understood from the following description of several embodiments of the invention when read in conjunction with the accompanying drawings.

BEST MODE FOR CARRYING OUT THE INVENTION

Figure 1:
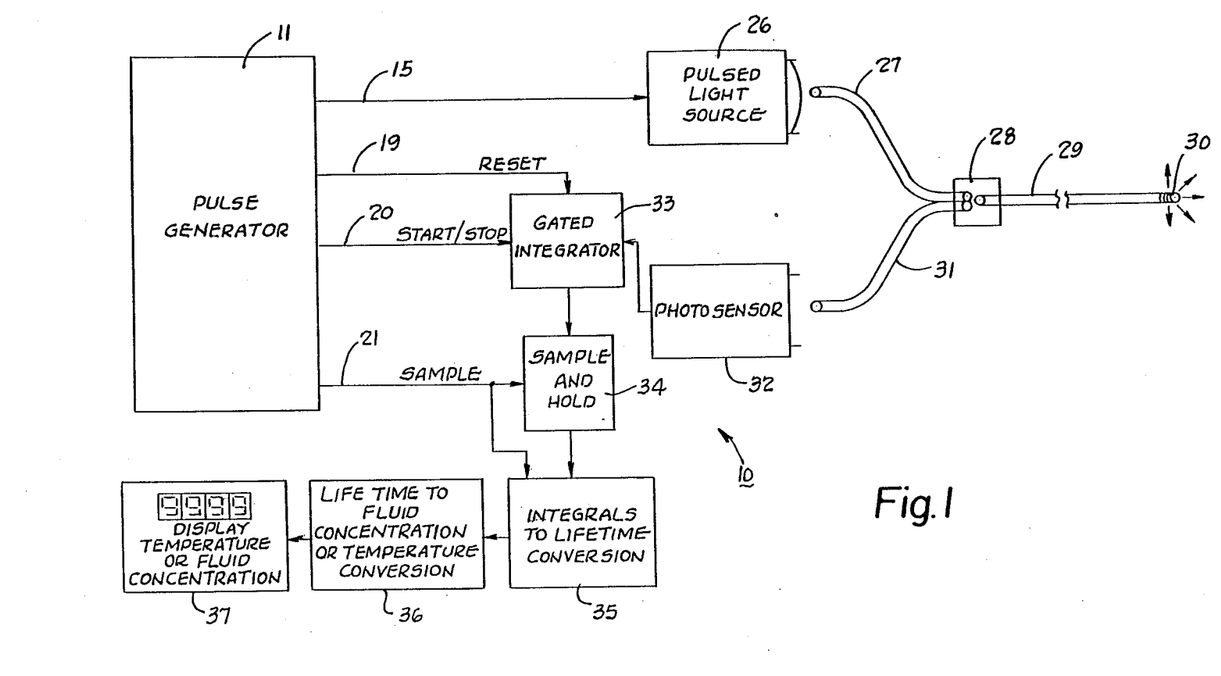
FIG. 1 is a block diagram of a fluorometric sensor system according to the present invention.
Figure 10:
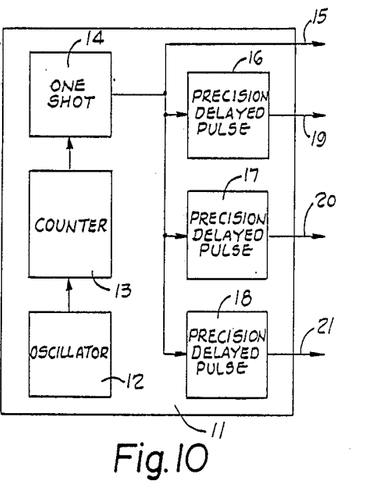
FIG. 10 is a detailed block diagram of one embodiment of a pulse generator according to the present invention.

Referring now to FIG. 1, there is shown a pulse generator 11 having four outputs 15, 19, 20, 21 for producing time-related output pulses which control the operation of a fluorometric sensor system 10. A more detailed diagram of one embodiment of the pulse generator 11 is shown in FIG. 10, wherein an oscillator 12, counter 13, and one-shot 14, (digital logic components) provide a timed-pulse 15 governing the cyclic rate of the system operation. For each occurance of the timing pulse 15, a set of 3 precision pulse delay timers 16, 17, and 18 provide time-delayed pulses 19, 20, and 21 which may have precise but arbitrarily predetermined time-delays and pulse widths with respect to the triggering pulse 15.

Referring again to FIG. 1, the timing pulse output 15 governs the operation of a pulsed light source 26, which has at least a portion of its light output in the upper portion of the visible or long ultraviolet spectrum. At least a portion of the light output pulse is conveyed via a first light path 27 to a bi-directional coupler/connector 28, and thence through a catheter 29 made from or containing a fiber optic light pipe to a fluorometric sensor 30.

The fluorometric sensor 30 is a photoluminescent body of material which has been deposited at the end of the fiber optic light pipe 29, and which responds to the pulses of light from the pulsed light source 26 by emitting a fluorescent light emission having a decay rate and average lifetime that is sensitively modified by a quenching fluid component or the temperature in the environment of the fluorometric sensor. Average lifetime is defined as the time required for the sensor's fluorescence to decline to a value of $1/e$ of its initial excited intensity.

A portion of said fluorescent emissions are conveyed via catheter 29, coupler/connector means 28, and a second light path 31 to a photosensor 32. The photosensor's output signal faithfully follows the fluorescent decay of the fluorometric sensor, said time-varying output being analyzed by a gated integrator 33 and a sample and hold circuit 34 which are turned on and off by time-related output pulses 19, 20, and 21 from pulse generator 11.

The output signal from the sample and hold circuit 34 represents, during one period of the cycle, the integral of a portion of the fluorescent decay curve during a predetermined time window in relationship to the light output of the pulsed light source 26. During a second period of the cycle, the output of the sample and hold ciruit 34, represents the integral of the photosensor baseline noise and offset during a second predetermined time window.

An integral to lifetime conversion circuit 35 subtracts the baseline integral from the decay curve integral to obtain a signal indicative of the lifetime of the fluorometric sensor 30. The lifetime signal is converted to a fluid concentration or temperature in a circuit 36 which take into account the nonlinear nature of the bimolecular quenching phenomenon and temperature compensation of the fluorometric sensor 30. A display of fluid concentration or temperature is generated by a display unit 37.

Figure 2:
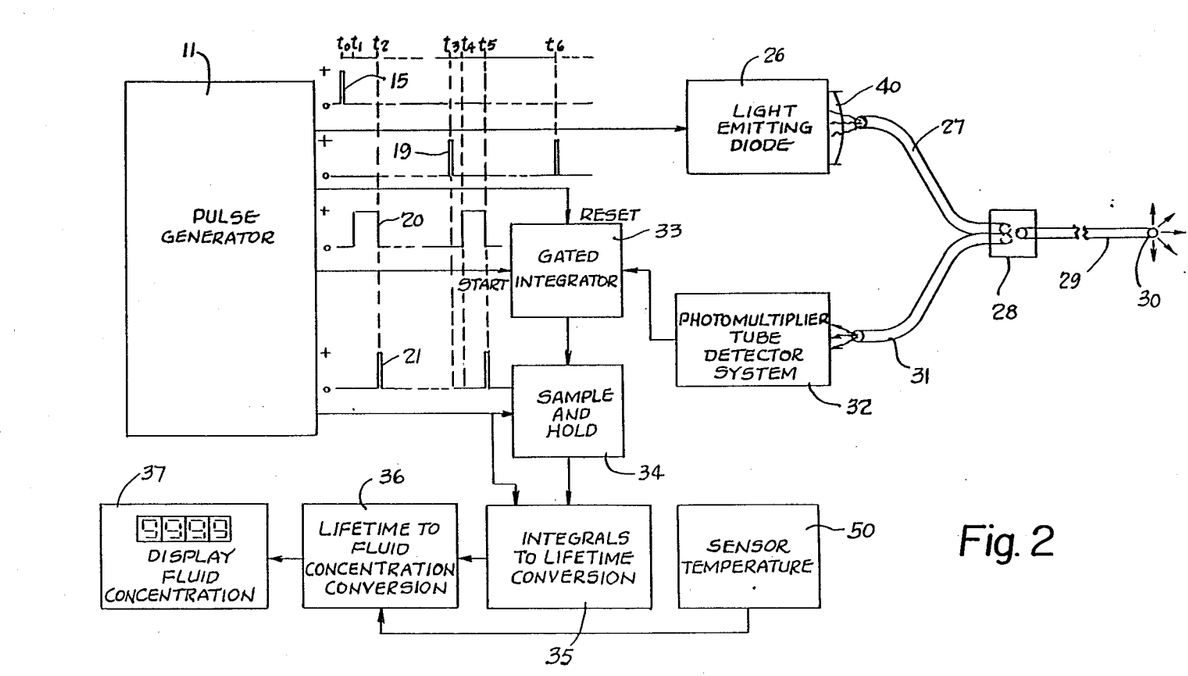
FIG. 2 is a schematic diagram of one embodiment of the invention.
Figure 9:
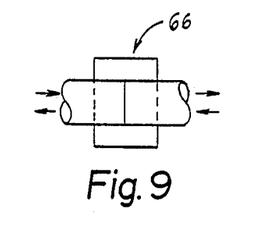
FIG. 9 is an enlarged view of another embodiment of a fiber optic coupler means according to the present invention.

Turning now to FIG. 2, there is shown a detailed schematic of one embodiment of the present invention. The pulse generator 11 generates a short output pulse 15 at time $t_o$. The output pulse 15 triggers a light emitting diode 26, such as SIEMENS CORPORATION #LDB-5410, which emits blue light suitable for excitation of fluorometric sensors to be later described. A laser diode or a laser-diode-pumped solid state laser may also be used without departing from the spirit of the present invention. The resulting light output of the LED 26 is shown as the cross-hatched rectangle starting at $t_o$ in FIG. 3, and terminating prior to $t_l$. A portion of the output from the LED is focued via a lens 40 into fiber optic light pipe 27 and thence travels to the coupler/connector 28. The coupler may optionally be of a "fused" type, wherein all of the components are permanently fixed into place, or of a demountable type, wherein the catheter 29 may be removed and replaced. As a third alternative, the coupler may be of a "fused" type, with a separate in-line fiber-optic connector, as illustrated in FIG. 9, being used to replace or exchange the catheter 29.

Figure 8:
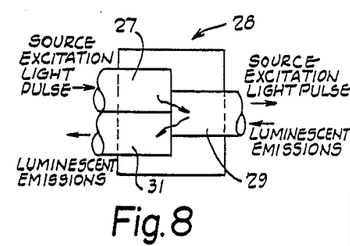
FIG. 8 is an enlarged view of one embodiment of a bi-directional coupler/connector means according to the present invention.

The operation of the coupler/connector 28 is best shown in FIG. 8, wherein light excitation pulses from the LED are conveyed into the catheter 29 and then to the fluorometric sensor 30 located at or near its tip, at the termination of the light pipe. The fluorometric sensor 30 includes a luminescent material deposited at or near the tip of the catheter as has been described in the prior art (see, for instance Lubbers, Re. 31,879, Stevens, U.S. Pat. No. 3,612,866, Quick, U.S. Pat. No. 4,223,226), one of the most suitable types being the fluophor/polymer sensor described in published U.K. patent application No. 2132348A, entitled "Method and Apparatus for Oxygen Determination" to Demas et al.

One suitable fluorometric oxygen sensor 30 consists of the fluophor tris (4.7-diphenly-1,10-phenanthroline) ruthenium (II) complex ion in a solution of approximately 1% by weight with a silicon polycarbonate copolymer (Petrarch Systems—No. PS254—"Petrarch MB", BRISTOL, PA.) containing approximately 45% silicon and 55% polycarbonate by weight. A silcon - alpha methylstyrene copolymer—(PS096) from the same supplier may also be used as the polymer constituent with very good results.

The fluophor and the polymers are commonly soluble in methylene chloride, and are mixed in dissolved form to the desired proportions, whereupon the prepared mixture can be cast into blocks, sheets, or films, and the methylene chloride evaporated out of the matrix in a bell jar containing methylene chloride vapors. The solvent vapor pressure in the jar is slowly reduced to zero over several hours resulting in a controlled escape of solvent from the matrix. This process ensures clear, uniform solid solutions of the fluophor and polymer.

Figure 3:
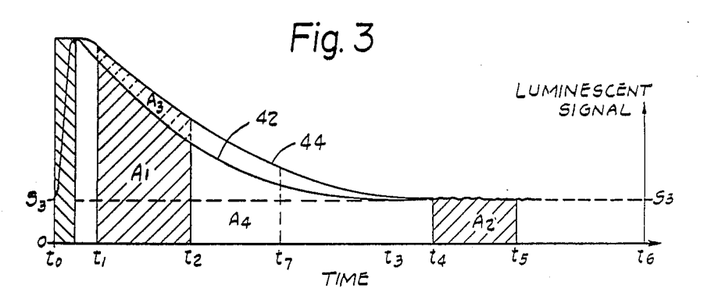
FIG. 3 is a timing diagram depicting events during the analysis of a fluorescent decay in the embodiment shown in FIG. 2.
Figure 7:
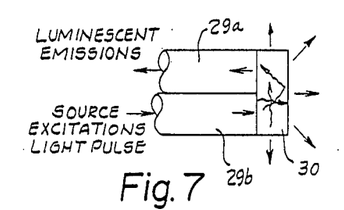
FIG. 7 is an enlarged view of an alternate embodiment of the catheter tip and fluorometric sensor according to the present invention.

The excitation pulse 15 causes the fluorometric sensor 30 to produce a fluorescent output having a decay response which is approximately exponential, as illustrated by a first curve 42 in FIG. 3, and which persists well beyond the extinction of the excitation pulse 15. The fluorescent decay response and lifetime is sensitively modified by a change in the fluid components (quencher) concentration or temperature in the environment of the sensor. For instance, if the quencher concentration or temperature in the environment of the fluorometric sensor 30 should subsequently decrease, the average fluorescent decay lifetime would be increased, as illustrated by a second fluorescent decay response curve 44 in FIG. 3. Increases in temperature or fluid component concentration would have a similar but opposite effect on the fluorescent decay curve. A portion of the fluorescent response, along with scattered light from the excitation light pulse, is conveyed back through catheter 29, through bi-directional coupler/connector 28, and via fiber optic light pipe 31 to a photomultiplier tube detector system 32. Optionally, the catheter and sensor may be constructed using separate light pipes 29a, 29b (FIG. 7) for conveyance of source excitation and fluorescent emissions and separate fiber optic connectors as shown in FIG. 9 may be used to connect the catheter to the rest of the system. Notwithstanding which of the above fiber-optic interconnect schemes is used, the photomultiplier tube detector 32 produces a time-varying output signal indicative of curve 42 shown in FIG. 3. Note that curve 42 does not return to zero after the fluorescent decay has ended at $t_6$, but instead returns to a positive baseline $S_3$, representing the dark current of the photomultiplier tube and the offset of any in-line signal amplifiers. This baseline $S_3$ may change with time and with the operating temperature of the instrument. To make the system independent of photomultiplier tube operating characteristics, these baseline variations are accounted for in the signal processing technique described below.

The gated integrator 33 is maintained in a "zero" state and ignores the output of the photomultiplier tube 12 until time $t_l$, thus ignoring photomultiplier tube output from scattered light generated by the pulsed light source 26. At time $t_l$, integrator 33 begins integration upon being switched on-line by output pulse 20 from pulse generator 1. The integrator continues until time $t_2$ at which time the integration is suspended by the termination of pulse 20.

An integrator 33 for use in the present invention can be quite simply constructed with an RC (resistor-capacitor) circuit, wherein FET transistors responsive to the Pulse Generator Pulses, are used to switch the RC circuit input and short the capacitor at appropriate times in the cycle. Since the photomultiplier tube (PMT) 32 acts as almost an ideal current source while operating in its linear region, the voltage developed across the capacitor which results from current flowing throught the resistor will be the integral of the PMT current during the period of integration.

Also at time $t_2$ (FIG. 3), a short pulse 21 from the pulse generator 11 instructs the sample and hold circuits 34 to obtain the value stored in the integrator 33. The integrals to lifetime conversion circuit 35 is also advised by pulse 21 that a new integral value is now available at the sample and hold circuit 34. The advantage of using a sample and hold circuit 34 for conveyance of the integral from the integrator 33 to the circuit 35 is that if the integrator 33 is of the RC type described above, the integral is quickly obtained and fixed before any "droop" in the voltage across the capacitor occurs; and the integrator can thus be reset in preparation for a new integration. Sample and hold 34 thus has a constant output to the circuit 35 between times $t_2$ and $t_5$ representing integral $A_1$, as illustrated in FIG. 3.

At time $t_3$ the gated integrator 33 is reset by pulse 19 from the pulse generator 11 and a second integration cycle occurs between times $t_4$ and $t_5$. The second integral, represented by $A_2$ in FIG. 3 is locked into the sample and hold 34 at time $t_5$, and the integrator is reset at time $t_6$ in preparation for a new cycle. Each new cycle is identical to that previously described, and is initiated by a pulse 15 from the signal generator 11.

The integrals to lifetime conversion circuit 35 is alternatively presented with two signals from the sample and hold circuit 34, the first representing $A_1$, the integral of the fluorescence decay curve plus baseline offset between times $t_1$ and $t_2$, and the second representing $A_2$, the integral of the baseline offset only during a similar time interval. Although the described embodiments measure the baseline offset during each pulse generator cycle, it may be more convenient or efficient to measure the offset component only at greater time intervals or randomly, as the stability needs of the system dictate. $A_2$ is subtracted from $A_1$, to obtain a signal which can be converted to the lifetime of the fluorometric sensor, for instance using the following relationship:

$$A_1 - A_2 = K \left[ \frac{T(e^{-t_o/T})(1 - {}^{-t_e/T})^2}{(1 - e^{-t_c/T})} \right] \quad (1)$$

where:

$A_1 - A_2$ = integral from $t_1$ to $t_2$ minus baseline integral
$K$ = a constant of proportionality
$T$ = the lifetime of the sensor
$e$ = natural logirhythm
$t_d$ = time from termination of light pulse to $t_1$.
$t_e$ = $time$ $t_1$ to $t_2$
$t_c$ = cycle time between $t_o$'s The above equation assumes an expodential decay and can be solved for T by a successive approximation computer program. Small deviations from a truly exponential curve do not seriously hamper accuracy when using this computation method, and even if the decay is not exponential, a useful signal indicative of temperature or fluid concentration is obtained.

A reduction in quencher concentration at the tip of the catheter causes a corresponding increase in the lifetime of the sensor 30, as is best illustrated by decay curve 44 in FIG. 3. The integral obtained between time $t_1$ and $t_2$ will now become the sum of $A_1$ and $A_3$, thus becoming geater. This increase in integral signal will be interpreted as an increase in lifetime, according to the relationship previously described.

The lifetime signal is then conveyed to a lifetime to fluid concentration conversion circuit 36 wherein the lifetime is related to quencher concentration at the tip of the catheter according to the theoretical relationship for bimolecular quenching described by STERN and VOLMER, but modified for the purpose of the present invention as follows:

$$\frac{T_o}{T} = \{1 + K_g T_o [Q]\}^N \quad (2)$$

where:
$T_o$ = lifetime in absence of quencher
$T$ = lifetime in the presence of a given concentration [Q] of quencher
$K_g$ = bimolecular quenching constant
[Q] = quencher concentration
N = linearizing constant A particular problem occurs, however, with this stage in the analysis in that virutally all fluorometric sensors which are sensitively quenched by (and therefore are useful for measurement of) fluid components such as the hydrogen ion or the oxygen molecule are also responsive to changes in temperature, due to the inherent physics of the bi-molecular quenching process, and the changing solubilities of such chemical species in fluid media.

No methods of compensating for this "dual" sensitivity have been described in the prior art which would render such devices most useful under conditions of changing fluid or body temperature.

The lifetime to fluid concentration conversion circuit 36 resolves the above-mentioned problem by treating the above "constants" $T_o$, $K_g$ and N as variables which change in a predetermined and predictable manner as the temperature of the fluorometric sensor changes. The sensor temperature is obtained by a separate sensor 50 system located in the environment of the fluorometric sensor. Such a temperature measurement system 50 may be constructed from a thermistor, a thermocouple, or from a separate fluorometric sensor apparatus. Alternately, the body temperature may be measured with a thermometer, the temperature of the fluorometric sensor estimated thereby, said estimate being input manually into the system. Lifetime to fluid concentration conversion circuit 36 then applies the correct values of $T_o$, $K_g$, and N based upon internally stored data such that the modified Stern Volmer equation has the appropriate constants for the sensor's current operating temperature.

If the fluorometric sensor system is responsive only to changes in temperature, however, the lifetime to fluid concentration conversion circuit 36 may use the well known relationship:

$$T = \frac{a}{e^{-b/KT}} \quad (3)$$

where:
T = lifetime
a and b = constants for the material
e = natural log rhythm
K = Boltzman's constant
T = Temperature in degrees kelvin.
to relate the sensor lifetime to the temperature at the tip of the catheter.

The resulting fluid concentration or temperature signal from the circuit 36 is then displayed on a display 37.

Figures 4, 5:
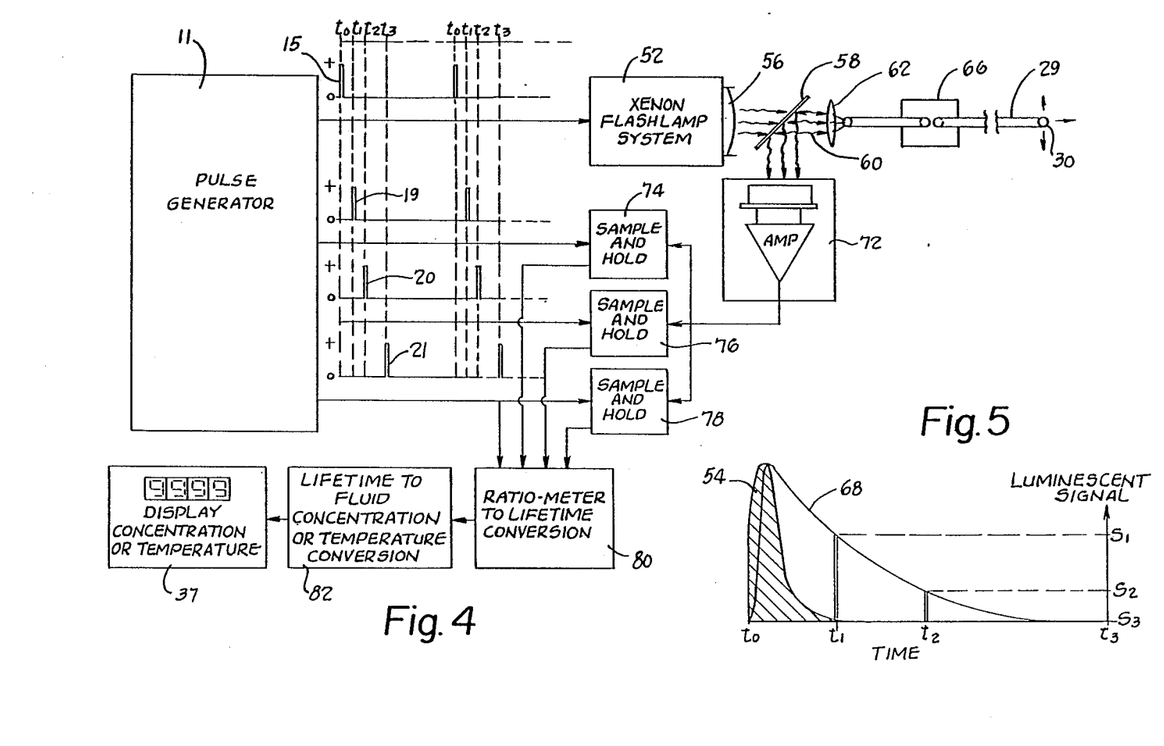
FIG. 4 is a schematic diagram of another embodiment of the invention.
FIG. 5 is a timing diagram depicting events during the analysis of the fluorescent decay in the embodiment shown in FIG. 4.
Figure 6:
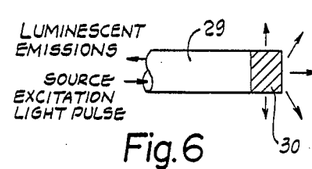
FIG. 6 is an enlarged view of one embodiment of a catheter tip and fluorometric sensor according to the present invention.

Turning now to FIG. 4, there is shown a schematic diagram of an alternative embodiment of the invention. Pulse generator 11 produces a short output pulse 15, at time $t_o$, which is used to trigger an electrical discharge in a xenon flashlamp system 52. A resulting light pulse 54, (shown in FIG. 5) from the flashlamp 52 is rich in blue and ultraviolet light suitable for exciting the fluorometric sensor 30. The output light is collimated by a lens 56, crosses a partially-mirrored beamsplitter 58, thence via a path 60 enters a focusing lens 62 and is focused to an intense spot at the proximal end of a light pipe 64, is conveyed through fiber optic connector 66 (as also illustrated in FIG. 9) and into catheter 29 whereupon it strikes fluorometric sensor 30. The resulting fluorescent emission decay is illustrated as a curve 68 in FIG. 5. A portion of the fluorescent decay along with scattered light from the light pulse, is conveyed via catheter 29, connector 66, interconnecting light pipe 64, lens 62, and path 60 to beamsplitter 58, whereupon a portion of said fluorescent emission is reflected along a path 70 to a photosensor 72.

In this embodiment, the photosensor 72 comprises a silicon photodiode and amplifier. The output current from the photosensor 72 between time $t_o$ and $t_1$ (see FIG. 5) is representative of the additive intensity of both the scattered light from the light pulse 22 and the initial fluorescent decay curve 68. If the scattered light intensity is very strong during this time segment, it can overload the amplifier. This difficulty can be avoided by limiting the output of the photodetector, for instance with silicon diodes since the photosensor need not accurately reproduce the intensity of the scattered light during time period $t_o$ to $t_1$. However, at time $t_1$, the scattered light pulse has dissipated to a small fraction of the fluorescent intensity and analysis of the decay curve can begin. A sample and hold circuit 74 is triggered by pulse 19 from the pulse generator 11 and acquires Sample 1 ($S_1$—see FIG. 5). Two other sample and hold circuits 76, 78 likewise acquire samples $S_2$ and $S_3$ of the fluorescent decay curve at predetermined time intervals $t_2$, $t_3$ after $t_1$. Time $t_3$ is chosen sufficiently long enough after $t_1$ so that the fluorescent decay curve has decayed to a small fraction of its initial intensity, regardless of the fluorometric sensor's lifetime. $S_3$, then, represents the positive baseline output of the photosensor as earlier described, whereas $S_1$ and $S_2$ are two sample points having a predetermined time relationship on the fluorescent decay curve.

In the event that the xenon flashlamp 52 exhibits some amount of variable turn-on delay or "jitter", a second photosensor may be employed to directly view the light output of the flashlamp, and thereby establish time $t_o$ as the instant that significant light output begins to emanate from the flashlamp. The output of this second photosensor would then be fed back into the pulse generator 11 as a "trigger" signal for generation of time-related pulses 19, 20, 21.

At time $t_3$, a ratio meter to lifetime conversion circuit 80 receives the pulse 21 and acquires samples $S_1$, $S_2$, and $S_3$ from the above-described sample-and-hold circuits 74, 76, 78 respectively. The circuit 80 then evaluates the following expression to develop a signal which is functionally related to the lifetime of the fluorometric sensor:

$$\frac{S_1 - S_2}{S_2 - S_3}$$

The analysis thereby takes into consideration the baseline "wander" of the photosensor and amplifier due to temperature and aging effects.

In the event that the fluorescent decay curve is very noisy, the value of the above expression will vary considerably from cycle to cycle. The ambiguity can be resolved if the circuit 80 develops a time-weighted average of the lifetime signal, which is then conveyed to lifetime to a fluid concentration or temperature conversion circuit 82.

In both the FIG. 3 and FIG. 5 illustrations a baseline or steady state measurement is obtained and subtracted from a signal obtained during the decay portion of the sensor's fluorescent output. One need not wait until the baseline portion of the curve is reached, however, to characterize the fluorescent lifetime. In the FIG. 3 example, one can determine an integral $A_4$ beginning at time $t_2$ and ending at time $t_7$. This integral $A_4$ can begin before the first integral $A_1$ has ended. The ratio of the two integrals $A_4/A_1$ uniquely characterizes the fluorescent lifetime of the probe. As noted above, even if the assumption of an exponential decay is not totally accurate useful lifetime information is obtained.

It will be understood that the above specific descriptions and drawings have been given for purposes of illustration only and that variations, modifications, and other combinations of the illustrations and specifications herein described can be made by those skilled in the art without departing from the spirit and scope of the appended claims.

I claim:

1. A measurement system for analysis of fluid concentration of a component inside a body, comprising:
    pulse generator means for generating a number of time related pulses;
    a fiber-optic equipped catheter for measuring a fluid component concentration; said catheter having a length to extend to a region of interest within a body while a proximal end portion of said catheter remains outside the body and including at least one fluorometric sensor in communication with one or more fiber optic light pipes within said catheter, said fluorometric sensor producing a fluorescent output in response to a light input, said fluorescent output having a fluorescent decay indicative of said fluid concentration in an environment of said fluorometric sensor;
    temperature sensing means for monitoring a temperature in the vicinity of the body and producing a temperature signal;
    light source means responsive to one or more of said pulses to generate pulses of output light, and for directing a portion of said light into said proximal end portion of said fiber-optic light pipe-equipped catheter;
    a photosensor positioned relative to the proximal end portion for sensing the fluorescent output of said fluorometric sensor conveyed to the proximal end portion by one of said fiber optic light pipes;
    sampling means for sampling an output of the photosensor at two or more predetermined times after initiation of a pulse of said output light to provide two or more fluorescent decay signals; and
    analysis means for analyzing said fluorescent decay signal of said sampling means to obtain a lifetime signal related to the fluid concentration of the component in the environment of the fluorometric sensor; and
    processing means for presenting a visual indication of the fluid component concentration by using the lifetime signal in a relation correlating the lifetime signal to component concentration of the form:

$$\frac{T_o}{T} = 1 + K_g T_o [Q]$$

where:
$T_o$ = lifetime in absence of fluid component
T = measured lifetime in the presence of a given concentration [Q] of fluid component
$K_g$ = bimolecular quenching factor
[Q] = fluid component concentration
and wherein the processing means includes temperature compensation means responsive to the temperature signal to adjust values of $T_o$, and $K_g$ with changes in the temperature in the vicinity of the body sensed by the temperature sensing means.

2. The apparatus according to claim 1, wherein said analysis means for analyzing the fluorescent decay signals performs an analysis technique wherein at least a portion of a fluorescent decay curve is integrated over a predetermined time to provide a decay curve integral functionally related to the lifetime of the fluorometric sensor.

3. The apparatus according to claim 2, wherein the analysis means begins decay curve integration at a predetermined time after light output from the light source means begins.

4. The apparatus according to claim 2, wherein a baseline output of the fluorometric sensor is also integrated and subtracted from said decay curve integral to develop a signal which is functionally related to the lifetime of the fluorometric sensor.

5. The apparatus according to claim 1, wherein at least one of the signals represents a baseline output of the photosensor in the absence of a light signal.

6. The apparatus according to claim 1, wherein said fluid component is an oxygen or a hydrogen ion.

7. The apparatus according to claim 6, wherein said fluorometric sensor is a fluophor/polymer matrix.

8. The apparatus of claim 7, wherein said matrix comprises a luminescent organometallic compound which is copolymerized, dissolved, or diffused into a polymer plastic or mixture of polymer plastics.

9. The apparatus of claim 8, wherein said luminescent organometallic compound is tris (4,7 diphenyl 1,10 phenthroline) Ruthenium II complex ion, or fluoresceinamine.

10. The apparatus of claim 9, wherein said polymer is chosen from the group: silicon rubber, a copolymer of silicon and polycarbonate, a copolymer of silicon and polystyrene, or an ion exchange resin.

11. A measurement system for analysis of fluid concentration of a component inside a body, comprising:

pulse generator means for generating a number of time related pulses;

a fiber-optic equipped catheter for measuring a fluid component concentration; said catheter having a length to extend to a region of interest within a body while a proximal end portion of said catheter remains outside the body and including at least one fluorometric sensor in communication with one or more fiber optic light pipes within said catheter, said fluorometric sensor producing a fluorescent output in response to a light input, said fluorescent output having a fluorescent decay indicative of said fluid concentration in an environment of said fluorometric sensor;

temperature sensing means for monitoring a temperature in the vicinity of the body and producing a temperature signal;

light source means responsive to one or more of said pulses to generate pulses of output light, and for directing a portion of said light into said proximal end portion of said fiber-optic light pipe-equipped catheter;

a photosensor positioned relative the proximal end portion for sensing the fluorescent output of said fluorometric sensor conveyed to the proximal end portion by one of said fiber optic light pipes;

sampling means for sampling an output of the photosensor at two or more predetermined times after initiation of a pulse of said output light to provide two or more fluorescent decay signals; and analysis means for analyzing said fluorescent decay signals of said sampling means to obtain a lifetime signal related to the fluid concentration of the component in the environment of the fluorometric sensor; and processing means for presenting a visual indication of the fluid component concentration by using the lifetime signal in a relation correlating the lifetime signal to component concentration of the form:

$$\frac{T_o}{T} = \{1 + K_g T_o [Q]\}^N$$

where:
$T_o$ = lifetime in absence of fluid component
T = measured lifetime in the presence of a given concentration [Q] of fluid component
$K_g$ = bimolecular quenching factor
[Q] = fluid component concentration
N = linearizing factor and wherein the processing means includes temperature compensation means responsive to the temperature signal to adjust values of $T_o$, $K_g$ and N used in the relation with changes in the temperature in the vicinity of the body sensed by the temperature sensing means.

12. The apparatus according to claim 1, wherein said analysis means for analyzing the fluorescent output performs an analysis technique wherein at least a portion of a fluorescent decay curve is integrated over time to provide a decay curve integral functionally related to the lifetime of the fluorometric sensor.

13. The apparatus according to claim 12, wherein said decay curve is integrated over a predetermined time interval.

14. The apparatus according to claim 12, wherein the analysis means begins decay curve integration at a predetermined time after light output from the light source means begins.

15. The apparatus according to claim 12, wherein a baseline output of the fluorometric sensor is also integrated and subtracted from said decay curve integral to develop a signal which is functionally related to the lifetime of the fluorometric sensor.

16. The apparatus according to claim 1, wherein at least one of the signals represents a baseline output of the photosensor in the absence of a light signal.

17. The apparatus according to claim 1, wherein said fluid component is an oxygen or a hydrogen ion.

18. The apparatus according to claim 17, wherein said fluorometric sensor is a fluophor/polymer matrix.

19. The apparatus of claim 18, wherein said matrix comprises a luminescent organometallic compound which is copolymerized, dissolved, or diffused into a polymer plastic or mixture of polymer plastics.

20. The apparatus of claim 19, wherein said luminescent organometallic compound is tris (4,7 diphenyl 1,10 phenthroline) Ruthenium II complex ion, or fluoresceinamine.

21. The apparatus of claim 20, wherein said polymer is chosen from the group: silicon rubber, a copolymer of silicon and polycarbonate, a copolymer of silicon and polystyrene, or an ion exchange resin.

22. A method for analyzing fluid component levels in a body comprising the steps of:

positioning a probe that fluoresces in response to incident light near a distal end of a fiber optic light pipe equipped catheter, said probe emitting a diminished fluorescent signal in the presence of the fluid component;

sensing a temperature in the vicinity of the body;

inserting the catheter into the body to position the probe in a body region of interest, sending a pulse of light through the catheter to excite the probe;

monitoring light returning from the probe to determine a fluorescent lifetime of the probe by sampling light output at multiple times subsequent to exciting the probe, ascribing an exponential decay to said light output, and determining from said multiple samples a sensed fluorescent lifetime;

correlating the sensed fluorescent lifetime with a fluid component concentration by using the sensed fluorescent lifetime in a relation correlating the sensed fluorescent lifetime with fluid component concentration of the form:

$$\frac{T_o}{T} = 1 + K_g T_o [Q]$$

where:
$T_o$ = lifetime in absence of fluid component
T = sensed lifetime in the presence of a given concentration [Q] of fluid component
$K_g$ = bimolecular quenching factor
[Q] = fluid component concentration while adjusting one or more of the values of $T_o$, and $K_g$ used in the relation as the temperature of the body changes.

23. A method for analyzing fluid component levels in a body comprising the steps of:
   positioning a probe that fluoresces in response to incident light near a distal end of a fiber optic light pipe equipped catheter, said probe emitting a diminished fluorescent signal in the presence of the fluid component;
   sensing a temperature in the vicinity of the body;
   inserting the catheter into the body to position the probe in a body region of interest;
   sensing a pulse of light through the catheter to excite the probe;
   monitoring light returning from the probe to determine a fluorescent lifetime of the probe by sampling light output at multiple times subsequent to exciting the probe, ascribing an exponential decay to said light output, and determining from said multiple samples a sensed fluorescent lifetime;
   correlating the sensed fluorescent lifetime with a fluid component concentration by using the sensed fluorescent lifetime in a relation correlating the sensed fluorescent lifetime with fluid component concentration of the form:

$$\frac{T_o}{T} = \{1 + K_g T_o [Q]\}^N$$

where:
   $T_o$ = lifetime in absence of fluid component
   $T$ = sensed lifetime in the presence of a given concentration [Q] of fluid component
   $K_g$ = bimolecular quenching factor
   [Q] = fluid component concentration
   N = linearizing factor
   while adjusting one or more of the values of $T_o$, N, and $K_g$ used in the relation as the temperature of the body changes.

24. The method of claim 23 wherein the monitoring step is performed by converting a light output from the catheter to an electrical signal and integrating the electrical signal over time to determine a fluorescent lifetime.

* * * * *

UNITED STATES PATENT AND TRADEMARK OFFICE
CERTIFICATE OF CORRECTION

PATENT NO. : 4,895,156
DATED : January 23, 1990
INVENTOR(S) : JOHN E. SHULZE

It is certified that error appears in the above-identified patent and that said Letters Patent is hereby corrected as shown below:

On the title Page Item (76):
The correct spelling of the inventor's name is: JOHN E. SHULZE Column 1, line 66, "specie" should be -- species --.

Signed and Sealed this

Thirty-first Day of March, 1992

Attest:

HARRY F. MANBECK, JR.

*Attesting Officer*     *Commissioner of Patents and Trademarks*